United States Patent [19]

Spohn

[11] Patent Number: 4,487,713

[45] Date of Patent: Dec. 11, 1984

[54] PRODUCTION OF ISOCYANATES FROM ESTERS OF AROMATIC CARBAMIC ACIDS (URETHANES)

[75] Inventor: Ralph J. Spohn, Woodcliff Lake, N.J.

[73] Assignee: Exxon Research & Engineering Co., Florham Park, N.J.

[21] Appl. No.: 343,584

[22] Filed: Jan. 28, 1982

Related U.S. Application Data

[63] Continuation-in-part of Ser. No. 277,733, Jun. 26, 1981, abandoned, which is a continuation of Ser. No. 179,064, Aug. 18, 1980, abandoned.

[51] Int. Cl.³ ............................................. C07C 118/00
[52] U.S. Cl. ................................................ 260/453 P
[58] Field of Search ..................................... 260/453 P

[56] References Cited

U.S. PATENT DOCUMENTS

| | | | |
|---|---|---|---|
| 2,409,712 | 10/1946 | Schweitzer | 260/453 P |
| 3,054,819 | 9/1962 | Barclay, Jr. et al. | 260/453 P |
| 3,870,739 | 3/1975 | DeLaMater et al. | 260/453 P |
| 3,919,278 | 11/1975 | Rosenthal et al. | 260/453 P X |
| 3,919,279 | 11/1975 | Rosenthal et al. | 260/453 P |
| 3,919,280 | 11/1975 | Rosenthal et al. | 260/453 P |
| 3,936,484 | 2/1976 | Rosenthal et al. | 260/453 P |
| 3,962,302 | 6/1976 | Rosenthal et al. | 260/453 P |
| 4,081,472 | 3/1978 | Tsumura et al. | 260/453 P |
| 4,146,727 | 3/1979 | Shawl et al. | 260/453 P |
| 4,163,019 | 7/1979 | Mango | 260/453 P |
| 4,307,029 | 12/1981 | Takeuchi et al. | 260/453 P |

FOREIGN PATENT DOCUMENTS

| | | |
|---|---|---|
| 1247451 | 9/1971 | United Kingdom . |
| 1458595 | 12/1976 | United Kingdom . |

OTHER PUBLICATIONS

Dyer, et al., J.A.C.S., 81, (1959), pp. 2138-2143, and 80, (1958), pp. 5495-5498.

*Primary Examiner*—Joseph Paul Brust
*Attorney, Agent, or Firm*—R. A. Maggio

[57] ABSTRACT

A process for converting aromatic carbamates to their corresponding isocyanates by thermolysis at a pressure of at least atmospheric in the presence of a catalyst selected from Ti, Sn, Sb, and Zr is disclosed.

10 Claims, No Drawings

PRODUCTION OF ISOCYANATES FROM ESTERS OF AROMATIC CARBAMIC ACIDS (URETHANES)

CROSS REFERENCE TO RELATED APPLICATIONS

The present application is a continuation-in-part application of U.S. patent application Ser. No. 277,733 filed June 26, 1981, now abandoned, which is a continuation of U.S. patent application Ser. No. 179,064 filed Aug. 18, 1980, now abandoned.

BACKGROUND OF THE INVENTION

The present invention is directed to processes for converting aromatic carbamates and polymeric aromatic carbamates to their corresponding isocyanates by thermolysis in the presence of a specifically defined catalyst at atmospheric or super atmospheric pressures.

Isocyanates are very useful substances as starting materials for polyurethanes. Such polyurethanes can be used in the formation of a variety of products ranging from automative parts to thermal insulation. The properties of the final polyurethane end product is to a large extent determined by the number of isocyanate groups i.e., (—NCO) present on the isocyanate starting material. For example, difunctional isocyanates do not result in crosslinking and are useful in the production of flexible polyurethane foams. Polyfunctional isocyanates result in crosslinking and consequently are useful in the production of rigid polyurethane foams. Within the class of polyfunctional isocyanates is a subclass of isocyanates, namely, polymeric aromatic polyisocyanates, which have gained market recognition and are possessed of unique properties which render them particularly adaptable for specialized end uses such as the manufacture of urethane adhesives. The term, "polymeric isocyanates" as used herein refers to a mixture of compounds containing poly alkylene or arylene poly aryl isocyanate oligomers such as poly methylene poly phenyl isocyanate (described hereinafter in more detail).

Non-polymeric aromatic isocyanates include such compounds as tolylene diisocyanate, methylene-bis-(4-phenyl isocyanate) and naphthylene diisocyanate.

A current process for preparing these nonpolymeric isocyanates, for example, tolylene diisocyanate of the formula:

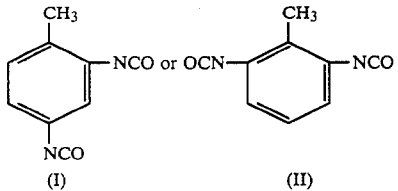

(I) (II)

comprises nitrating toluene to form dinitrotoluene, reducing the latter with hydrogen to form the corresponding diamine and then reacting the diamine with phosgene. Thus, the aforedescribed process comprises complicated and troublesome steps, requiring the use of a large amount of highly toxic phosgene and permitting the formation of hydrogen chloride as by-product.

An alternative approach to preparing non-polymeric isocyanates involves the synthesis of carbamates from nitro compounds and subsequently pyrolyzing carbamates to form the isocyanate and an alcohol co-product.

The reaction for forming isocyanates by pyrolysis of carbamates may be shown by the following basic equation:

$$RHNCO_2R' \rightarrow RNCO + R'—OH \tag{1}$$

On thermal dissociation of the carbamate, several undesirable side reactions take place at the same time. These side reactions are: the decarboxylation reaction of the carbamate accompanying the formation of a primary amine $RNH_2$ and an olefin or of a secondary amine RNHR as a by-product; the reaction between the produced isocyanate and the starting carbamate, permitting the formation of an allophanate as by-product; the reaction between the produced isocyanate and an amine formed as by-product permitting the formation of a urea compound as by-product; and the polymerization of the produced isocyanate, permitting the formation of an isocyanurate or a polymer as by product. The thermal dissociation reaction of equation (1) above is reversible and its equilibrium remains with the left-hand side carbamate at low temperature but is shifted to the right-hand side by heating, whereby the dissociation of the carbamate takes place. In this case, the thermal dissociation temperature varies according to the sort of carbamate and the reaction conditions. Accordingly, it is important for obtaining isocyanates advantageously from carbamates to perform the pyrolysis reaction of equation (1) selectively while inhibiting the above mentioned side and reverse reactions.

The probability of certain undesirable side reactions occurring is increased as the reaction temperature is increased and as the time during which the isocyanate product remains in contact with the components of the reaction mixture is increased. As one lowers the reaction temperature, however, the reaction rate decreases, along with the solubility of the carbamate in any solvent used in the reaction medium.

The conventional pyrolysis of carbamates can be roughly classified into reactions carried out in the vapor phase at a high temperature and reactions carried out in the liquid phase at a relatively low temperature. U.S. Pat. No. 3,734,941 discloses a typical vapor phase process wherein a carbamate is pyrolyzed at 400°–600° C. in the presence of a Lewis acid and the resultant vapor is separated by fractional condensation into an isocyanate and an alcohol. According to this process, for example, tolylene diisocyanate is obtained in a yield of 60% by pyrolysis of diethyl tolylene-2,4-dicarbamate of the formula:

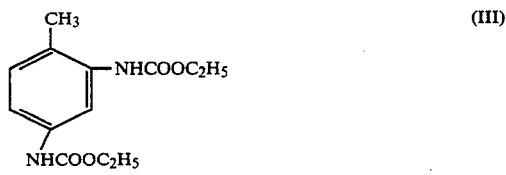

in the presence of ferric chloride. However, this process has the drawbacks of a low yield of the product, decomposition of the catalyst, corrosion of the reaction apparatus at high temperatures, and formation of a considerable amount of a polymer as by-product. (See also Br. Patent Spec. No. 1,247,451).

German Pat. No. 2,410,505 proposes as an improved vapor phase method, a process wherein the residence time of the reactants at 350°–550° C. is controlled within 15 seconds. According to this process, the yield of isocyanate is as high as 93%, although the carbamate has to be supplied in the form of powders to the reaction zone. However, a solid polymer is also formed by this process as by-product and is gradually deposited in the reactor and in the condenser during the course of sustained operation, thus making it difficult to conduct a continuous reaction. In addition, a large quantity of heat required for the endothermic pyrolytic reaction has to be supplied to the starting material within a very short period of time. This additional factor causes this process to encounter great difficulty in being adopted into practice.

Liquid phase processes were developed in an attempt to lower the reaction temperature and reduce undesirable side reactions.

For example, U.S. Pat. No. 2,409,712 discloses the pyrolysis of N-substituted carbamic esters in the liquid phase, in the presence or absence of a diluent, at temperatures of 150° to 350° C. under a high vacuum to distill the resulting isocyanate overhead. None of the carbamic esters disclosed include polymeric aromatic carbamates. Consequently, not only does the use of high vacuum add to the cost of the process, but the use of high vacuum if applied to the distillation of polymeric isocyanates would be ineffective due to the very high boiling points of the latter. This patent also does not disclose the use of catalysts as described herein.

In an article in the Journal of the American Chemical Society, Vol. 81, page 2138 et seq. (1959), Dyer et al show that ethyl carbanilate gives phenyl isocyanate (60–75 mole percent based on carbinilate degraded) and ethyl alcohol when heated for 6 hours at 200° C. under pressure sufficiently low (60–120 mm Hg) to vaporize the alcohol but high enough to retain the isocyanate. At atmospheric pressure no phenylisocyanate is obtained, although 70 percent of the ethyl carbanilate is destroyed. At 250° C. and atmospheric pressure alpha-methylbenzylcarbanilate gives major amounts of aniline, alpha-methylbenzyl aniline, styrene and carbon dioxide.

U.S. Pat. No. 3,054,819 discloses the pyrolysis of an aliphatic mono carbamate and dicarbamate esters in the optional presence of a basic catalyst such as alkali and alkaline earth metal oxides, hydroxides, carbonates and the like. The pyrolysis is conducted at subatmospheric pressures and at temperatures of 100° C. to 300° C. In accordance with this process the isocyanate product must be separated from the glycol ester co-product preferably by distilling isocyanate alone or in combination with the glycol ester and separating the two co-products. Either alternative is not available with polymeric aromatic isocyanates. Thus, this patent fails to disclose (1) the use of aromatic carbamates of any kind, and (2) the use of the catalysts of the present invention in conjunction with any carbamates.

U.S. Pat. No. 3,919,278 is directed to a process for preparing isocyanates wherein a mononuclear aromatic carbamate is dissolved in an inert solvent in an amount such that the total concentration of the carbamate and a product obtained by pyrolysis thereof is within a range of about 1–20 mole % and the pyrolysis of the carbamate is carried out at 230°–290° C. in the presence of an inert carrier used in an amount of at least 3 molar proportion to the carbamate. Polymeric aromatic carbamates are not mentioned in this patent nor is the use of the catalysts of the present invention in conjunction with any carbamates.

U.S. Pat. No. 3,919,279 is directed to a process for preparing isocyanates wherein a carbamate is dissolved in an inert solvent and brought into contact at a high temperature (i.e. 175°–350° C.) with a catalyst composed of a heavy metal (Mo, V, Mn. Fe, Co, Cr, Cu or Ni) or a compound thereof to effect the pyrolysis of the carbamate at temperatures of 175° to 350° C. The concentration of the carbamate dissolved in the inert solvent is less than 80%, by weight, e.g. between about 3 and about 80%, by weight, 3% being the lower limit of solubility of the carbamate in the solvent. This patent emphasizes the importance of maintaining the carbamate in a substantially completely dissolved state at reaction temperature during conversion to the isocyanate to minimize the formation of polymerization products such as tars or resins as well as undesirable by-products. Product alcohol is removed from the reaction mixture in the examples at atmospheric or superatmospheric pressure. The patent fails to disclose the catalysts described herein for the present invention or the thermolysis of polymeric aromatic carbamates.

U.S. Pat. No. 3,962,302 is directed to a process for producing isocyanates by thermolysis of carbamates while dissolved in an inert organic solvent and in the absence of a catalyst. Reaction temperatures range from 175° to 350° C. (preferably 200° to 300° C.) at carbamate concentrations of between 3% and 80%, by weight, of the reaction solution. This patent fails to disclose the thermolysis of polymeric aromatic carbamates and the use of catalysts of the present invention with any carbamates.

U.S. Pat. No. 4,081,472 is directed to a process for preparing aromatic isocyanates by the thermolysis of an aromatic carbamate at temperatures of 150° to 350° C. (preferably 200° to 300° C.) under substmospheric pressure in the presence of a catalyst dissolved in an inert solvent. The resultant isocyanate and alcohol must be removed in vapor form during the reaction and thereafter separately condensed (See Col. 5 lines 55 et. seq. and Col. 9 lines 27 et. seq.). Consequently, the process must be conducted at subatmospheric pressure. Suitable catalysts include compounds of Cu, Zn, Al, Sn, Ti, V, Fe, Co, and Ni. While it is disclosed as being desirable to dissolve the carbamate in a solvent, the process can be performed with the carbamate in the suspended or emulsified state (Col 8, lines 20 et. seq.). This patent does not disclose the thermolysis of polymeric aromatic carbamates or the thermolysis of aromatic carbamates at atmospheric or superatmospheric pressures.

U.S. Pat. No. 4,146,727 discloses a method for preparing dicarbamates and polymeric carbamates. In this patent it is suggested (See Col. 1 lines 25 et seq. and Col. 4 lines 56 et. seq.) that the polymeric carbamates described therein can be thermally decomposed in a solvent to their corresponding polymeric isocyanates in accordance with two of the aforenoted patents, namely, U.S. Pat. Nos. 3,919,279 and 3,962,302, notwithstanding the lack of detail in either of these two patents as described above, or the U.S. Pat. No. 4,146,727 patent, as to how this can be achieved.

U.S. Pat. No. 4,163,019 discloses a process for preparing 4,4′-alkylidene diphenyl diisocyanate by a two step process involving the condensation of a phenyl alkyl carbamate using an aldehyde or ketone to form a dimer, e.g., dicarbamate, and an exchange reaction wherein a phenyl isocyanate is mixed with the dicarbamate to form a phenyl alkyl carbamate and the corresponding diisocyanate. Certain tin compounds are disclosed as being suitable exchange catalysts. This reference does not disclose a use of these catalysts for the thermolytic cracking of carbamates in the absence of an exchange reaction.

An article in Chemical Week, Nov. 9, 1977, pp. 57–58 discloses a process which comprises the steps of reacting nitrobenzene, carbon monoxide and an alcohol to form corresponding urethanes (alkyl phenyl carbamates). The reaction product is reacted with formaldehyde to produce a condensate which contains p,p'-methylene diphenyl dialkylcarbamate and higher oligomers. This product is, in turn, thermally split into the corresponding "polymeric diisocyanates" and alcohol, which is recycled. The set of reactions is reported to involve the use of high temperatures in the range between 100° and 200° C. in the first reaction step and between 200° and 300° C. in the decomposition step and the reaction leads to a mixture of polymeric diisocyanates. This article does not disclose the use of the catalysts described herein for the present invention.

There are several difficulties which one encounters in attempting to conduct thermolysis of polymeric aromatic carbamates. Such polymeric materials are much less soluble in common solvents than non-polymerics. Consequently, even slight side reactions such as between isocyanate and carbamate reduce the solubility of the polymeric reaction product even further than would otherwise result from similar reactions using non-polymeric reactants. Once the polymeric material starts to insolubilize, the formation of tars, gums and other undesired by-products begins to accelerate. Low reaction temperatures also decrease the decomposition reaction rate requiring longer reaction times. Longer reaction times can provide more opportunity for undesirable side reactions to take place, although at a slower rate. If the reaction temperature is raised to increase the reaction rate and the solubility of the polymeric reactants and/or products and by-products, other undesirable side reactions begin to take place at an accelerated pace at these elevated temperatures. Furthermore, if the concentration of polymeric carbamate is too high in solution, the polymeric isocyanate product (which is non-volatile at reaction conditions and cannot be economically removed from the reaction medium by vaporization) will react more readily with the polymeric carbamate to form an allophonate which is even more insoluble than either the polymeric reactants or product isocyanate thereby destroying the reaction sequence. Diluting the reactants with solvent reduces the economic efficiency of the process and requires greater capital investment in plant equipment.

Consequently, a balance must be established between reaction temperature, and polymeric carbamate concentration and solubility to permit the process to be run economically. Accordingly and in view of the above there has been a continuing search for ways to reduce the decomposition reaction temperature of polymeric carbamates without sacrificing the reaction rate to any great extent or alternatively to increase the reaction rate at similar temperatures employed in the absence of a catalyst. A reduction in reaction temperature would decrease undesirable side reactions induced by more elevated temperatures. Increasing the reaction rate provides less time for undesirable side reactions to take place until product removal.

Regarding non-polymeric aromatic carbamates, the aforedescribed prior art clearly indicates that conventional disclosed reaction temperatures for the thermolysis of the carbamates to form the corresponding isocyanates varies from about 175° to 350° C. at atmospheric or supra atmospheric pressures. Accordingly, there has also been a continuing search for ways to either reduce reaction pyrolysis temperatures of non-polymeric aromatic carbamates below 175° C. to reduce undesired condensation reactions which occur at elevated temperatures and thereby increase selectivity to the isocyanate, or alternatively to increase non-polymeric aromatic carbamate decomposition reaction rate at conventional pyrolysis temperatures to reduce the average reactant residence time in a reactor thereby permitting a reduction in capital investment in plant equipment (e.g. by reducing reactor size).

The present invention was developed in response to the aforedescribed searches.

SUMMARY OF THE INVENTION

In one aspect of the present invention, there is provided a process for producing at least one aromatic isocyanate from at least one aromatic carbamate. These carbamates are described herein and include polymeric as well as non-polymeric aromatic carbamates. This process is conducted by heating a mixture or solution of at least one of said carbamates in the presence of a metal containing catalyst said metal being selected from the group consisting of Ti, Sn, Sb, Zr and mixtures thereof, under conditions and in a manner sufficient to convert said carbamate to at least one isocyanate, and at least one alcohol, said heating being conducted at a pressure of at least atmospheric; and separating said alcohol from said isocyanate and recovering the isocyanate from the solution.

DESCRIPTION OF PREFERRED EMBODIMENTS

In accordance with the present invention aromatic carbamates are thermally decomposed into their corresponding isocyanate and alcohol in the presence of at least one catalyst.

The aromatic carbamates employed in the present invention can be categorized into non-polymeric aromatic carbamates and polymeric aromatic carbamates.

Non-polymeric aromatic carbamates (i.e. esters of a carbamic acid) which can be employed in the process of the present invention are represented by the structural formula:

$$R_1(\text{NHCOOR}_2)_n \qquad (IV)$$

wherein $R_1$ is a mono, di- or trivalent (preferably mono- or divalent) aromatic hydrocarbyl group containing typically from about 6 to about 32 (e.g. 6 to 22), preferably from about 6 to about 18 (e.g. 6 to 14) and most preferably from about 6 to about 10 (e.g. 6) carbon atoms. $R_1$ may contain an isocyanato group or a mono or divalent substituent not reactive with an isocyanato group. $R_2$ in structural formula IV is selected from monovalent: saturated-aliphatic, saturated-alicyclic, or aromatic hydrocarbyl group having typically not greater than 10 (e.g. 8) carbon atoms, preferably not greater than 6 carbon atoms and most preferably not greater than 4 (e.g. 2) carbon atoms, and may contain an isocyanato group or a monovalent substituent not reactive with an isocyanato group. Also in structural formula IV, n is a number of typically from 1 to 3, preferably 1 to 2, and most preferably 1, and corresponds to the valency of the $R_1$ group.

Illustrative of the substituent $R_1$ are aryl groups such as phenyl, tolyl, xylyl, naphthyl, biphenylyl, anthryl, phenanthryl, terphenyl, naphthacenyl, pentacenyl and methylene biphenyl groups and the divalent or trivalent groups formed by removing one or two hydrogen atoms respectively from these aromatic groups. These aromatic groups may contain an isocyanato group; a substituent not reactive therewith, such as an alkyl, typically $C_1$ to $C_5$ alkyl group, a halogen atom, nitro group, cyano group, an alkoxy group typically $C_1$ to $C_5$ alkoxy, an acyl group, an acyloxy group or an acylamido group; or a divalent substituent of similar nature, such as a methylene group, an ether group, a thioether group, a carbonyl group or a carboxyl group.

Examples of the substituent $R_2$ include aliphatic groups, such as methyl, ethyl, propyl, butyl, pentyl, hexyl, heptyl, octyl and methoxyethyl groups and alicyclic groups, such as a cyclohexyl group.

Representative examples of the carbamates utilizable in the present invention include methyl —N-phenylcarbamate, ethyl phenylcarbamate, propyl phenylcarbamate, butyl phenylcarbamate, octyl phenylcarbamate, ethyl naphthyl-1-carbamate, ethyl anthryl-1-carbamate, ethyl anthryl-9-carbamate, diethyl anthrylene-9,10 dicarbamate, ethyl p-biphenylyl carbamate, diethyl m-phenylenedicarbamate, diethyl naphthylene-1,5-dicarbamate, methyl p-tolylcarbamate, ethyl p-trifluoromethylphenylcarbamate, isopropyl-m-chlorophenylcarbamate, ethyl 2-methyl-5-nitrophenylcarbamate, ethyl 4-methyl-3-nitrophenylcarbamate, ethyl 4-methyl-3-isocyanatophenylcarbamate, methylene-bis(phenyl-4-methylcarbamate), dimethyl tolylene-2,4-dicarbamate, diethyl tolylene-2,4-dicarbamate, diethyl tolylene-2,6-dicarbamate, diisopropyl tolylene-2,4-dicarbamate, dibutyl tolylene-2,4-dicarbamate, diphenyl tolylene-2,4-dicarbamate, diphenyl tolylene-2,6-dicarbamate, di(ethoxyethyl) tolylene-2,4-dicarbamate, diethyl 4-chlorophenylene-1,3-dicarbamate, methyl p-butoxyphenylcarbamate, ethyl p-acetylphenylcarbamate, ethyl o-nitrophenylcarbamate, isopropyl m-trifluoromethylphenylcarbamate, and trimethyl-N-phenyltricarbamate. Of these carbamate compounds, the most practical examples are the tolylenedicarbamates, naphthylenedicarbamates, methylene-bis-(phenylcarbamates) and mixtures thereof.

The polymeric aromatic carbamates which can be employed in the process of the present invention comprise a mixture of carbamates, the components of said mixture being represented by the structural formula:

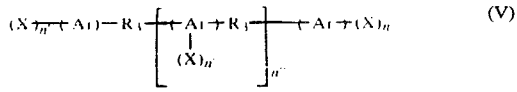
(V)

wherein: X represents the monovalent group —NHCO$_2$R$_2$, R$_2$ being as defined in connection with structural formula IV above; R$_3$ is independently selected from (a) a divalent straight or branched chain saturated aliphatic group having typically from about 1 to about 10, preferably from about 1 to about 5, and most preferably from about 1 to about 2 carbons, (b) a divalent saturated alicyclic group having typically from about 4 to about 10, preferably from about 5 to about 8, and most preferably from about 6 to about 8 carbons, and (c) a divalent aromatic group having typically from about 6 to about 18, preferably from about 6 to about 14, and most preferably from about 6 to about 10 carbons; n' is a number of from about 1 to about 4, preferably from about 1 to about 3, and most preferably from about 1 to about 2 (e.g. 1); Ar is a substituted or unsubstituted aromatic hydrocarbyl group, typically an aromatic hydrocarbyl group having from 6 to 14, preferably 6 to 10, and most preferably 6 carbons, exclusive of substituents, said substituents being selected from halogen (i.e., F, Cl, Br and I), —NH$_2$, and mixtures thereof; and n" is a number which can vary from 0 to about 5 or higher on any individual carbamate in the mixture and the number average value of n" for all the carbamates in the mixture typically will vary from about 2.0 to about 3.5, preferably from about 2.2 to about 3.0, and most preferably from about 2.5 to about 2.8. All of the aforenoted polymeric aromatic carbamates are believed to be conventional in the art.

Representative examples of suitable R$_2$ and R$_3$ groups in structural formula V associated together in a single carbamate include the following:

| R$_2$ | R$_3$ |
| --- | --- |
| methyl | methylene |
| methyl | dimethylene |
| methyl | trimethylene |
| methyl | methyethylene |
| methyl | ethylethylene |
| methyl | 2,2-dimethyltrimethylene |
| methyl | 2-methyltrimethylene |
| methyl | 1,3-cyclopentylene |
| methyl | 1,4-cyclohexylene |
| methyl | 1,4-phenylene |
| ethyl | methylene |
| ethyl | dimethylene |
| ethyl | 2,2-dimethyltrimethylene |
| isopropyl | methyl |
| isopropyl | trimethylene |
| isopropyl | 1,4-phenylene |
| cyclopentyl | methylene |
| phenyl | methylene |

The most preferred R$_2$ group is methyl since it will form an alcohol co-product having the lowest boiling point.

The most preferred polymeric aromatic carbamate is a mixture of poly-N-lower alkyl (e.g., C$_1$ to C$_4$) —polymethylene polyphenyl carbamates.

In structural formula V, the identity of the substituents on the aromatic hydrocarbyl group can be controlled to be halogen in a manner effective to impart fire retardancy to the ultimate polyurethane into which the isocyanate derived from the carbamate is incorporated. Moreover, some of these substituents in structural formula V can be residual —NH$_2$ groups depending on and left over from, the method used to prepare the polymeric carbamate.

Methods for preparing non-polymeric aromatic carbamates are well known in the art and need not be commented on further. The preparation of polymeric aromatic carbamates can be conducted in accordance with U.S. Pat. Nos. 4,146,727; 4,172,948; and 4,202,986, the disclosures of which are herein incorporated by reference.

The catalyst which is employed to facilitate the thermolysis reaction comprises at least one metal, preferably utilized in the form of at least one metal containing polar compound, preferably polar organo compound, said metal being selected from the group consisting of Ti, Sn, Sb, Zr and mixtures. For homogeneous reactions these metal containing compounds are preferably selected in conjunction with a suitable inert organic solvent such that the metal moiety (with which the catalytic activity is associated) is soluble therein. Accordingly, the nonmetal moiety of the catalyst compound preferably possesses at least one polar functional group sufficient to solubilize, in the liquid carbamate (i.e. nonsolvent embodiment) and/or solvent (i.e. solvent embodiment), a catalytic amount of metal as defined hereinafter. Accordingly, while the preferred method for solubilizing the metal catalyst is a metal polar organic compound, any other method for solubilizing the catalyst in an inert solvent can be employed.

Included within the scope of metal organic compounds are metal salts with aliphatic, alicyclic and aromatic carboxylic acids such as formic acid, acetic acid, lauric acid, stearic acid, oxalic acid, azelaic acid, naphthenic acid, tetrahydrophthalic acid, benzoic acid, phthalic acid and pyromellitic acid; metal alcoholates with aliphatic and alicyclic alcohols such as methanol, ethanol, propanol, butanol, octanol, dodecyl alcohol, benzyl alcohol, ethylene glycol, propylene glycol, polyethylene glycol, glycerol, pentaerythritol and cyclohexyl alcohol as well as the corresponding metal thioalcoholates; metal phenolates with monohydric or polyhydric phenol derivatives such as phenol, cresol, nonylphenol, catechol and hydroquinone as well as the corresponding metal thiophenolates; metal salts with sulfonic acids such as methanesulfonic acid, ethanesulfonic acid, dodecanesulfonic acid, cyclohexanesulfonic acid, benzenesulfonic acid, toluenesulfonic acid and dodecylbenzenesulfonic acid; metal chelates with chelating agents, for example, beta diketones such as acetylacetone and benzoylacetone, ketoesters such as ethyl acetoacetate and ethyl benzoacetate; metal carbamates with the carbamates defined as the starting material for the present invention as well as the corresponding metal thiocarbamates and dithiocarbamates; metal salts with compounds having anionic ligands such as nitric acid group, phosphoric acid group, boric acid group and cyanato group; and metal complexes of the above mentioned various metal salts with ligands having a noncovalent electron pair such as amines, phosphines, phosphites, nitriles and amides.

Representative examples of suitable catalysts include zirconium tetra 2,4-pentanedionate, tributoxy antimony, tetrabutoxy titanium, tetrapropoxy zirconium, tetraoctyloxy titanium and mixtures thereof.

A preferred class of catalysts contain tin. Such tin compounds preferably are organo-tin compounds represented by the structural formula:

$$(R_4)_{4-a}Sn(B)_a \qquad (VI)$$

wherein $R_4$ is a hydrocarbyl group independently selected from alkyl, typically alkyl having from about 1 to about 18, preferably from about 1 to about 10, and most preferably from about 1 to about 5 carbons, and aryl, typically aryl having from about 6 to about 14, preferably 6 carbons; B is independently selected from the group consisting of halogen (i.e. F, Cl, Br, I) preferably Cl, alkoxy, (i.e., —OR), typically alkoxy having from about 1 to about 8, preferably from about 1 to about 6, and most preferably from about 1 to about 4 carbons; alkanoyloxy (i.e.,

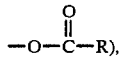

typically alkanoyloxy having from about 1 to about 8, preferably from about 1 to about 6, and most preferably from about 1 to about 4 carbons, oxo, and hydroxy; and "a" is an integer of from 1 to 3. The group ($R_4$) is preferably alkyl to enhance the volatility of the catalyst where desired.

Representative examples of suitable tin catalysts represented by structural formula VI include butyl-Sn (O)OH, dipropyl dimethoxytin, dibutyloxotin, tributylmethoxytin, triphenyl hydroxytin, trichloromethyltin, dibutyldimethoxytin, tributylmethoxytin, trimethylhydroxytin, dichlorodimethyltin, trimethylchlorotin, triphenylethanoyloxytin, diphenyldichlorotin and mixtures thereof. Inorganic halogenated tin compounds, such as tintetrachloride, and tindichloride, can also be employed.

Preferred catalysts include butyl-Sn(O)OH, dibutyloxotin, tributylmethoxytin, triphenylhydroxytin, trichloromethyltin, dibutyldimethoxytin, tributylmethoxytin, tintetrachloride, and mixtures thereof.

Metal compounds which have been found to possess ineffective catalytic activity include tetraethyltin (characterized by its lack of a polar functional group) dichlorotriphenyl antimony (characterized by the +5 valence state of antimony), and titanium dichlorodi-2,4-pentanedionate (characterized by extreme steric hinderance around the titanium metal moiety). Accordingly, in selecting a suitable catalyst, the immediately aforenoted characteristics preferably should be avoided to obtain a catalyst exhibiting effective activity.

The catalysts described herein, particularly the tin catalysts, have been found to substantially accelerate the initial thermal decomposition of aromatic carbamates to their corresponding alcohols up to a conversion of about 90%. This is extremely beneficial in terms of providing the option of conducting the reaction below conventional pyrolysis temperatures or of operating at conventional temperatures but producing product at a much faster rate thereby reducing the size of the reactor needed to produce similar quantities of isocyanate product obtained in accordance with conventional techniques. It is also an advantage of the present invention that the process using the aforedescribed catalysts is run at atmospheric (i.e., 14 psia) or super atmospheric pressures (e.g., 14 to 200 psia). The use of atmospheric pressure permits the use of more desirable solvents which have relatively low boiling points and which would otherwise be recovered with product at subatmospheric pressures necessitating additional separation steps. It also eliminates the need for expensive vacuum equipment.

The process of the present invention is conducted in the liquid phase by heating the carbamate, preferably a solution of the carbamate, in the presence of the aforedescribed catalyst. If no solvent is employed, the carbamate must be in the liquid state during the thermolysis reaction. This is achieved by selecting the reaction temperature to be above the carbamate melting point. To dissolve the carbamate, an inert organic solvent is preferably used. Any solvent which is stable at reaction temperature, i.e., will not decompose or react with any of the reactants, can solubilize the carbamate at reaction temperature, and which has a boiling point above, preferably at least 25° C. above, the reaction temperature at the reaction pressure can be employed.

Thus, the inert organic solvent functions to dissolve the carbamate as well as the resulting isocyanate at reaction temperature, and optionally, to dissolve the catalyst, and other by-products, if any. The inert organic solvent also functions to evenly disperse heat throughout the reaction mixture, and to dilute the carbamate and reaction products to the extent that undesirable side reactions are kept to a minimum subject to economic considerations. Preferably, the solvent will also solubilize the catalyst although the catalyst can be employed in a heterogeneous state, e.g., in supported form.

Suitable inert organic solvents include hydrocarbons, ethers, thioethers, ketones, thioketones, sulfones, esters, organo silane compounds, halogenated aromatic compounds and mixtures thereof.

Representative examples of suitable solvents include chlorobenzene, o-dichlorobenzene; diethylene glycoldimethylether, triethylene glycoldimethylether, tetraethylene glycoldimethylether (also referred to as tetraglyme), 1,6-dichloronaphthalene, methoxy naphthalene; aliphatic hydrocarbons such as the higher alkanes, dodecane, hexadecane, octadecane, and liquid paraffin; the corresponding alkenes; petroleum fractions of paraffin series such as those usually employed as lubricating oils or cutting oils; alicyclic hydrocarbons such as petroleum fractions of the naphthene series; aromatic hydrocarbons such as dodecylbenzene, dibutylbenzene, methylnaphthalene, phenylnaphthalene, benzylnaphthalene, biphenyl, diphenylmethane, terphenyl and aromatic petroleum fractions usually employed as rubber-treating oils; and substituted aromatic compounds having no reactivity with the isocyanate such as chloronaphthalene, nitrobiphenyl and cyanonaphthalene; esters and thioethers such as diphenyl ether, methylnaphthyl ether, diphenyl thioether and the like aromatic ethers and thioethers; ketones and thioketones such as benzophenone, phenyl tolyl ketone, phenyl benzyl ketone, phenyl naphthylketone and the like aromatic ketones or thioketones; sulfones such as diphenyl sulfone and the like, aromatic sulfones; esters such as animal and vegetable oils, dibutyl phthalate, dioctyl phthalate, phenyl benzoate and the like aliphatic and aromatic esters; organosilane compounds such as conventional silicone oils and materials thereof.

The preferred solvents include hexadecane, chlorobenzene, o-dichlorobenzene, diethyleneglycoldimethylether, triethyleneglycoldimethylether, tetraethyleneglycoldimethylether, dichloronaphthalene, methoxynaphthalene and mixtures thereof.

While any amount of solvent effective to perform the aforedescribed functions can be employed, such effective amounts typically will constitute from about 50 to about 98, preferably from about 50 to about 90, and most preferably from about 50 to about 80%, by weight, based on the combined weight of solvent and carbamate.

The amount of catalyst which is present during reaction, preferably dissolved in the solvent, is any amount effective to accelerate the pyrolysis reaction in relation to the uncatalyzed reaction. Thus, while any effective amount of catalyst can be employed, such effective amounts typically will constitute from about 0.001 to about 0.3 moles, preferably from about 0.01 to about 0.2 moles, and most preferably from about 0.01 to about 0.1 moles of catalyst metal, per mole of carbamate ester group on the carbamate.

The pyrolysis of non-polymeric aromatic carbamates is conducted at temperatures of from about 50° to about 200° C., (e.g., 80° to 200° C.), and preferably from about 80° to about 150° C., (e.g., 100° to 125° C.).

The pyrolysis of polymeric aromatic carbamates is conducted at a temperature of from about 50° to about 300° C., preferably from about 80° to about 250° C., (e.g., 80° to 180° C.), and most preferably from about 80° to about 150° C.

It is critical to the present invention that the pressure at which the pyrolysis reaction is run for either polymeric or non-polymeric aromatic carbamates be at least atmospheric. Supra atmospheric pressures can also be employed.

The reaction time for the pyrolysis of non-polymeric aromatic carbamates will vary depending on the particular carbamate selected, the reaction temperature employed, the type and amount of catalyst employed, and the particular mode of reaction. However, the reaction time is shortened by the catalyst of the present invention relative to the reaction time using no catalyst under similar reaction conditions up to a conversion of about 90%. Accordingly, for batch reactions conducted within the reaction conditions recited above, reaction times will typically vary from about 1 to about 120 minutes, preferably from about 1 to about 60 minutes, and most preferably from about 1 to about 15 minutes for non-polymeric aromatic isocyanates. Reaction times under similar conditions recited above for batch reactions employing polymeric aromatic isocyanates typically will vary from about 0.1 to about 120 minutes, preferably from about 0.5 to about 60 minutes, and most preferably from about 1 to about 15 minutes.

Reaction times for a continuous process will vary depending on the concentration of carbamate at various steps within the reaction sequence (e.g. if multiple reactions are employed).

As implied above, the process of the present invention can be conducted in either a batch wise or continuous manner. In a continuous process, for example, the carbamate, in powdery or molten form or as a mixture with inert solvent is supplied to at least one reactor which has previously been charged with a given catalyst and optionally additional inert solvent and has optionally been preheated to a selected reaction temperature and pressure. In the absence of a solvent, the reaction temperature must be sufficient to permit the thermolysis reaction to be conducted in the liquid phase, i.e., above the melting point of the carbamate feed and isocyanate product. Thus, a liquid phase can be achieved by dissolving the carbamate in a solvent as described herein or by melting the carbamate in the absence of a solvent. If the alcohol co-product is lower boiling than the isocyanate, as is preferably the case, then the alcohol can either be distilled from the solvent as formed or be removed by the assistance of an inert gas carrier (such as nitrogen, argon, carbon dioxide, methane, ethane, propane and mixtures thereof), being passed through the solution, such as through a fitted disc or similar means for dispersion or by the use of a solvent having a boiling point between the isocyanate and alcohol and distilling between the boiling points of the isocyanate and alcohol. By this means recombination of the isocyanates is minimized. The use of a carrier gas is particularly preferred in the absence of a solvent to facilitate alcohol product removal.

Alternatively, if the alcohol is higher boiling than the generated isocyanate the isocyanate can be recovered in a manner similar to that described above for the alcohol co-product. Where a polymeric aromatic isocyanate is formed this option is unavailable since the polymeric isocyanate is not volatile at reaction temperatures. In this instance, catalyst and solvent can be removed from the reaction mixture by any means capable of achieving this effect. For example, catalyst and solvent can be removed overhead by distillation. Thus, for this embodiment a catalyst is selected which is sufficiently volatile to vaporize at distillation temperatures. Alternatively, the solvent is removed overhead, and the catalyst removed from the reaction mixture by contacting the polymeric isocyanate with a suitable extraction solvent, e.g. hexadecane, in which the catalyst is preferentially soluble or which contains a complexing agent. It may even be commercially desirable to avoid removal of the catalyst from the polymeric isocyanate since these catlaysts can also be employed as catalysts in the formation of a polyurethane end product.

Desirably, the reaction conditions are controlled to achieve as high a degree of conversion as possible to avoid the need to separate unreacted polymeric carbamate from the polymeric aromatic isocyanate. This can be achieved by increasing the amount of catalyst and/or the degree of alcohol co-product removal. However, since the polymeric aromatic carbamate is less soluble in the solvents described herein than the polymeric aromatic isocyanate product, separation of polymeric carbamate from polymeric isocyanate product can be achieved by solvent extraction techniques which make use of these different solubilities when the reaction is conducted at low conversion. The virtual elimination of identifiable by-products make this technique extremely simple.

Unreacted carbamate can be collected and fed to a second reactor or recycled.

It has been further found that the process of the present invention performs increasingly better as the purity of the carbamate employed therein increases. In some instances commercially available carbamates may possess impurities which insolubilize during reaction in a disadvantageous manner.

The present invention for the pyrolysis of polymeric aromatic carbamates to the corresponding polymeric isocyanates can be incorporated into the multi-step process described in co-pending U.S. patent application Ser. No. 342,583, filed Jan. 23, 1982 of common assignee for the production of polymeric aromatic carbamates and isocyanates from alkylated aromatic compounds.

The aforesaid multireaction step process has the following sequential steps: ammoxidation of an alkylated aromatic compound to form a nitrile, hydrolysis of the nitrile to an amide, conversion of the amide to a carbamate via e.g., a Hoffman rearrangement, condensation of the carbamate with an aldehyde to form a polycarbamate, and optionally, decomposition of the polycarbamate to a polyisocyanate.

The invention disclosed and claimed herein has particular utility in the aforesaid multireaction process as an improved means for decomposition of the polymeric aromatic carbamate to the corresponding polymeric aromatic polyisocyanate.

The following examples are given as specific illustrations of the claimed invention. It should be understood, however, that the invention is not limited to the specific details set forth in the examples. All parts and percentages in the examples as well as in the remainder of the specification are by weight unless otherwise specified.

In the examples which follow unless specified otherwise, the equipment used to conduct the reaction consists of a 100 ml round bottomed indented three-necked flask equipped with a GlasCol TM high temperature heating mantle and magnetic stirbar. A thermometer is connected through an open-ended U-shaped tube to allow addition of reaction mixture components which are syringed in through a rubber septum on the other opening of the "U". The center neck is fitted with two, stacked, water-cooled 6" condensers through which the gases exit. The upper condenser has the ability to collect condensed liquids to prevent contamination of the reactor by potentially reintroducing condensed alcohol. Nitrogen is dried through a bed of Linde 4A TM molecular sieves after passing through a Drierite TM column and dispensed under the reaction liquid level. Gases exiting the reaction equipment also pass through a Drierite TM column which also has a slight positive nitrogen flow from a bubbler. This is to prevent air from entering the flask when the nitrogen addition tube is opened for sampling. The nitrogen rate is regulated with a Fisher-Porter Flowrater TM tube which has been calibrated against a wet-test meter. Temperature is controlled with an $I^2R$ thermowatch device.

EXAMPLE 1

The following example is intended to illustrate the effect of various catalysts on the first order rate constant for the pyrolysis reaction. The general procedure for conducting the reaction is as follows. To a dried nitrogen flushed flask as described above is charged 50 ml of solvent. The solvent (i.e. tetraglyme) is then preheated under atmospheric pressure to 200° C. and maintained thereat during the course of the reaction. To this flask is then added, over a period of 1-2 minutes, 5 g (31 mmoles) of methylenediphenylene dicarbamate (MDC) and sufficient catalyst to achieve about a 10 mole % concentration based on the moles of carbamate. Samples of isocyanate product are removed from the flask over time and quenched by adding them to a solution of dibutylamine (referred to herein as DBA) dissolved in tetraglyine solvent (10% DBA by weight of the solution) to form a urea derivative from the isocyanate present in each sample. This derivative, which is indicative of the moles of isocyanate formed is analyzed by a Hewlett-Packard 1084B high pressure liquid chromatograph (referred to herein as HPLC) on a $C_8$ reverse phase column using water and acetonitrile mobile phases. The last sample is taken after about 120 to 180 minutes of reaction. Sample analysis is also confirmed by infrared analysis of the product solution containing the isocyanate product and by comparison of the isocyanate in the sample with a control sample.

A linear plot is drawn of the log of isocyanate concentration (determined by HPLC analysis) versus time. From the slope of this linear plot the first order rate constant is determined. The first order rate constants for various catalysts employed in conjunction with MDC determined in accordance with the above procedures are summarized at Table 1. For control purposes one run is conducted in the absence of a catalyst.

TABLE 1

| Run No. | Catalyst* | First Order Rate Constant $K_1$ (min.$^{-1}$ at 200° C.) |
|---|---|---|
| 1 | None | .0134 |

TABLE 1-continued

| Run No. | Catalyst* | First Order Rate Constant $K_1$ (min.$^{-1}$ at 200° C.) |
|---|---|---|
| 2 | Bu$_2$Sn(OMe)$_2$ | .0247 |
| 3 | Sb(OMe)$_3$ | .0276 |

*Bu = Butyl
Me = Methyl

From the above rate constants, it can be seen that the catalysts substantially improve the rate of the pyrolysis reaction at 200° C.

EXAMPLE 2

To a nitrogen flushed 100 ml flask equipped as described above is charged at atmospheric pressure 4.58 g (30 m moles) of methyl-N-phenyl carbamate, 2.94 g of chlorobenzene as an internal standard, 0.89 g dibutyltin dimethoxylate as the catalyst and 25 ml of 1,2-dichloroethane as solvent. The solution is heated to reflux (88° C.) atmospheric pressure and 5.8 ml of solvent containing methanol is slowly distilled overhead over a period of 75 minutes. A sample of the undistilled product is analyzed by Gas Phase Chromatographic Analysis (hereinafter GPC). The sample analysis shows 5.2 m moles of phenylisocyanate is formed at a selectivity of 99 mole % and conversion of 17.3 mole %.

EXAMPLE 3

The procedure in Example 2 is repeated except for replacement of the 1,2-dichloroethane with toluene. The reaction is conducted for a period of 40 minutes at a temperature of 87° C. Toluene forms an azeotrope with methanol and facilitates its removal from the reaction mixture. The selectivity to phenylisocyanate is 99 mole % and the conversion is 33 mole %.

EXAMPLE 4

A 50 ml 3-necked flask equipped with a thermometer (with Thermowatch), a magnetic stirrer, a short path distillation head, and a nitrogen sparger is charged with 15.23 g methyl-N-phenyl carbamate and 0.8137 g dibutyl tin dimethoxylate. The mixture is heated at atmospheric pressure within the range of from 100° to 120° C. over 3 hours with nitrogen sparging. After 3 hours of reaction GPC analysis shows a selectivity to phenyl isocyanate of 99 mole % and a conversion of 40 mole %. After continued heating for an additional period of 3 hours, the selectivity is 95 mole % and the conversion is 44.3 mole %. On cooling, the solution separates into two phases (i.e. solid and liquid). To check for methanol removal, a small amount of methanol is added. The liquid phase became solid white and a 10° C. temperature exotherm is measured, thus indicating the presence of active isocyanate groups. This example demonstrates that the thermolysis reaction can be conducted in the absence of a solvent and that at initial high concentrations of feed carbamate, isocyanate product can be generated without the formation of undesirable by-products because of the reduced temperature employed and the sparging with nitrogen gas to facilitate alcohol removal. However, in the absence of a solvent, the carbamate must be in the liquid state at reaction conditions.

EXAMPLE 5

A solution of a 1.0 g of the dimethyl carbamate of methylene diphenylene diisocyanate is dissolved in 50 ml of 1,2-dichloroethane and heated at atmospheric pressure to reflux (88° C.). At reflux, 0.09 g of dipropyl tin dimethoxylate is added. GPC analysis of the product solution after 13 minutes of reaction shows a substantial conversion to the diisocyanate methylene diphenylene diisocyanate with no identifiable by-products. This example illustrates that the carbamate groups react independently and that conversion of one carbamate group to its corresponding isocyanate does not affect conversion of others in the same molecule. Consequently, the thermolysis reaction can be viewed as a series of first order reactions, with each carbamate functionality acting independently. This applies to any polyfunctional carbamate of the type described herein.

It also illustrates that the thermolysis reaction can be conducted at low temperatures, e.g. 88° C.

The principles, preferred embodiments, and modes of operation of the present invention have been described in the foregoing specification. The invention which is intended to be protected herein, however, it is not to be construed as limited to the particular forms disclosed, since these are to be regarded as illustrative rather than restrictive. Variations and changes may be made by those skilled in the art without departing from the spirit of the invention.

What is claimed is:

1. A process for producing at least one aromatic isocyanate from at least one aromatic carbamate represented by the structural formula selected from the group consisting of:

(I)

and

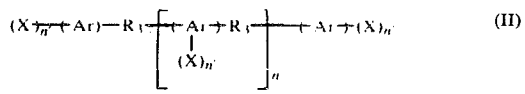

(II)

said structural formula II representing a mixture of carbamates and wherein in structural formula I: $R_1$ is a monovalent, divalent, or trivalent aromatic hydrocarbyl group containing from about 6 to about 32 carbon atoms; $R_2$ is a monovalent hydrocarbyl group selected from saturated-aliphatic, saturated-alicyclic, or aromatic, said hydrocarbyl group having not greater than about 10 carbon atoms; and n is a number of from 1 to 3 corresponding to the valency of $R_1$; and wherein in structural formula II: X is the monovalent group —NHCOOR$_2$ with $R_2$ being as defined in connection with structural formula I; $R_3$ is independently selected from the group consisting of (a) a divalent straight or branched chain saturated aliphatic group having from about 1 to about 10 carbon atoms, (b) a divalent saturated alicyclic group having from about 4 to about 10 carbon atoms, and (c) a divalent aromatic group having from about 6 to 14 carbon atoms; Ar is a substituted or unsubstituted aromatic hydrocarbyl group having from 6 to 14 carbon atoms, said substituents being selected from halogen, —NH$_2$, and mixtures thereof; and n" is a number, the number average value of which in said mixture can vary from about 2.0 to about 3.5, and n' is a number of from about 1 to about 4; which comprises:

(i) heating in the liquid phase at least one of said carbamates in the presence of a catalyst comprising at least one metal containing polar compound said metal being selected from the group consisting of Ti, Sn, Sb, Zr and mixtures thereof, under conditions and in a manner sufficient to convert by thermolysis said carbamate to at least one isocyanate, and at least one alcohol, said heating being conducted at a pressure of at least atmospheric and varying from 14 to about 200 psia, and said catalyst being effective to accelerate the thermolysis reaction rate relative to the thermolysis reaction rate in the absence of said catalyst, said heating being conducted at a temperature of from 80° to 150° C.; and (ii) separating said alcohol from said isocyanate and recovering the isocyanate.

2. The process of claim 1 wherein said heating is conducted by dissolving said carbamate and a metal catalyst containing polar organic compound into an inert organic solvent to form a solution and heating the solution.

3. The process of claim 2 wherein: the catalyst is represented by the structural formula $(R_4)_{4-a}Sn(B)_a$: wherein $R_4$ is a hydrocarbyl group independently selected from alkyl of from about 1 to about 18 carbons, and aryl of from about 6 to about 14 carbons; B is independently selected from the group consisting of halogen, alkoxy having from about 1 to about 8 carbons, alkanoyloxy having from about 1 to about 8 carbons, oxo, and hydroxy, and "a" is an integer of from 1 to 3; and the inert organic solvent is selected from the group consisting of hexadecane, chlorobenzene, o-dichlorobenzene, diethyleneglycol dimethylether, triethyleneglycol dimethylether, tetraethyleneglycol dimethylether, dichloronaphthalene, methoxynaphthalene, and mixtures thereof.

4. The process of claim 3 wherein the carbamate is represented by structural formula I.

5. The process of claim 3 wherein the carbamate is represented by structural formula II.

6. The process of claim 4 wherein the solution which is heated comprises from about 50 to about 98%, by weight, inert organic solvent, based on the combined weight of solvent and carbamate, and from about 0.001 to about 0.3 moles of metal in the catalyst per mole of carbamate ester group on the carbamate.

7. The process of claim 5 wherein the solution which is heated comprises from about 50 to about 98% by weight, inert organic solvent, based on the combined weight of solvent and carbamate, and from about 0.001 to about 0.3 moles of metal in the catalyst per mole of carbamate ester group on the carbamate.

8. The process of claim 5 wherein in the carbamate of structural formula II, $n'$ is 1, $R_3$ is methylene, and the average value for $n''$ is from about 2.2 to about 3.0.

9. The process of claim 8 wherein $R_2$ is methyl.

10. The process of any one of claims 1 and 2 wherein the catalyst is selected from the group consisting of zirconium tetra 2,4-pentanedionate, tributoxyantimony, tetrabutoxyantimony, tetrabutoxytitanium, tetrapropoxy zirconium, tetraoctyloxytitanium, butylhydroxyoxotin, dipropyldimethoxytin, dibutyloxotin, tributylmethoxytin, triphenylhydroxytin, trichloromethyltin, dibutyldimethoxytin, tributylmethyloxytin, trimethylhydroxytin, dichlorodimethyltin, trimethylchlorotin, triphenylethanoyloxytin, diphenyldichlorotin, tintetrachloride, tindichloride, and mixtures.

* * * * *